a reference

United States Patent
Kubinski et al.

(10) Patent No.: US 9,470,654 B2
(45) Date of Patent: Oct. 18, 2016

(54) SYSTEM AND METHOD FOR UPDATING A BASELINE OUTPUT OF A GAS SENSOR

(75) Inventors: David Kubinski, Canton, MI (US); Richard Soltis, Saline, MI (US); Jacobus H. Visser, Farmington Hills, MI (US); Yi Ding, Canton, MI (US); Michael Howard Parsons, Ann Arbor, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 1736 days.

(21) Appl. No.: 12/469,874

(22) Filed: May 21, 2009

(65) Prior Publication Data

US 2009/0223835 A1 Sep. 10, 2009

Related U.S. Application Data

(62) Division of application No. 11/297,153, filed on Dec. 7, 2005, now Pat. No. 7,578,925.

(51) Int. Cl.
*G01N 27/26* (2006.01)
*G01N 27/417* (2006.01)

(52) U.S. Cl.
CPC .................................. *G01N 27/417* (2013.01)

(58) Field of Classification Search
USPC .............. 204/406, 421–427; 205/780.5, 781, 205/782–786; 73/23.31, 23.32, 73/35.03–35.07, 114.01–114.69
See application file for complete search history.

(56) References Cited

U.S. PATENT DOCUMENTS

| | | | |
|---|---|---|---|
| 5,034,112 A | 7/1991 | Murase et al. | |
| 5,288,375 A | 2/1994 | Logothetis et al. | |
| 6,295,862 B1* | 10/2001 | Kurokawa et al. | 73/31.05 |
| 6,375,858 B1 | 4/2002 | Makigaki et al. | |
| 2002/0130053 A1 | 9/2002 | Ando et al. | |
| 2003/0164023 A1 | 9/2003 | Gruenwald et al. | |
| 2004/0238378 A1* | 12/2004 | Kumazawa et al. | 205/781 |
| 2007/0125665 A1 | 6/2007 | Kubinsky et al. | |

FOREIGN PATENT DOCUMENTS

| | | |
|---|---|---|
| EP | 0791827 | 2/1997 |
| EP | 0791828 | 2/1997 |

* cited by examiner

*Primary Examiner* — Luan Van
*Assistant Examiner* — Steven Rosenwald
(74) *Attorney, Agent, or Firm* — Julia Voutyras; Alleman Hall McCoy Russell & Tuttle LLP

(57) ABSTRACT

A method of operating a gas sensor is disclosed, wherein the sensor includes a pumping electrode configuration and a measuring electrode configuration, and wherein the method includes operating the sensor in a first mode in which a first, lower pumping potential sufficient to electrochemically remove an interfering compound from the sensor without electrochemically removing the analyte from the sensor is applied across the pumping electrode configuration and a measuring potential sufficient to electrochemically remove the analyte from the sensor is applied across the measuring electrode configuration; and operating the sensor in a second mode in which a second, higher pumping potential sufficient to electrochemically remove the analyte from the sensor is applied to the pumping electrode configuration.

7 Claims, 7 Drawing Sheets

SYSTEM AND METHOD FOR UPDATING A BASELINE OUTPUT OF A GAS SENSOR

CROSS REFERENCE TO PARENT APPLICATION

This present application is a divisional of U.S. patent application Ser. No. 11/297,153 filed Dec. 7, 2005, entitled "System and Method for Updating a Baseline Output of a Gas Sensor," naming David Kubinski, Richard Soltis, Jacobus H. Visser, Yi Ding, and Michael Howard Parsons as inventors, the entire contents of which are incorporated herein by reference.

BACKGROUND AND SUMMARY

Gas concentration sensors, such as $NO_x$ sensors, may be used in many different settings. For example, these sensors may be used in vehicles for monitoring concentrations of species in engine exhaust. As further improvement of combustion control is desired and emission regulations become more restrictive, the accuracy of these sensors becomes increasingly important. Unfortunately, the accuracy of these sensors may decrease with sensor aging due to a drift in the baseline output of the sensor.

One approach for obtaining an updated value for the baseline output is to measure the sensor output when there is known to be an absence of $NO_x$ in the exhaust gas. However, there may be an uncertainty regarding whether the analytical gas sample is sufficiently free of $NO_x$ when updating the baseline.

In one approach, the above issues may be addressed by a method of operating a gas sensor including a pumping electrode configuration and a measuring electrode configuration, the method comprising operating the sensor in a first mode in which a first, lower pumping potential sufficient to electrochemically remove an interfering compound from the sensor without electrochemically removing the analyte from the sensor is applied across the pumping electrode configuration and a measuring potential sufficient to electrochemically remove the analyte from the sensor is applied across the measuring electrode configuration, and operating the sensor in a second mode in which a second, higher pumping potential sufficient to electrochemically remove the analyte from the sensor is applied to the pumping electrode configuration. In some embodiments, a baseline output of the sensor may be determined while operating the sensor in the second mode.

DETAILED DESCRIPTION OF THE DEPICTED EMBODIMENTS

The present disclosure provides a method for updating a baseline output of a gas sensor. Generally, a baseline output of a sensor corresponds to an output of a sensor in the absence of a desired analyte. The methods disclosed herein may be used in any suitable sensor and application, including but not limited to the monitoring of species such as $NO_x$ in automotive exhaust.

Figure 1:
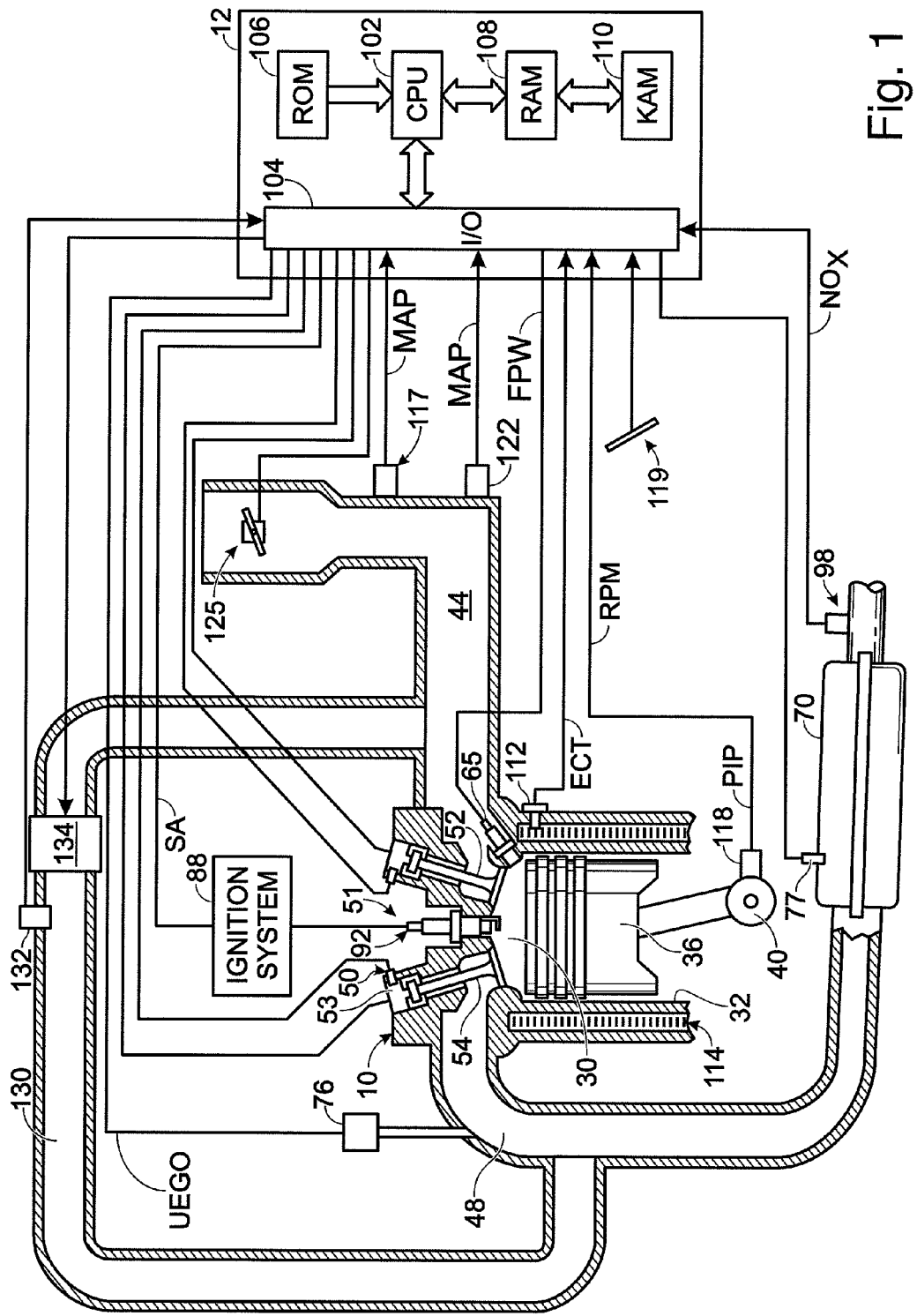
FIG. 1 is a schematic depiction of an exemplary embodiment of an internal combustion engine.

FIG. 1 shows an exemplary embodiment of an internal combustion engine 10, comprising a plurality of combustion chambers (one of which is indicated at 30), controlled by electronic engine controller 12. Combustion chamber 30 of engine 10 includes combustion chamber walls 32 with piston 36 positioned therein and connected to crankshaft 40. Combustion chamber 30 is shown communicating with intake manifold 44 and exhaust manifold 48 via respective intake valve 52 and exhaust valve 54. Fuel injector 65 is shown directly coupled to combustion chamber 30 for delivering liquid fuel directly therein in proportion to the pulse width of a signal (FPW) received from controller 12. However, in some embodiments, a fuel injector may be positioned in intake manifold 44, thereby providing port injection.

Intake air flow through intake manifold 44 may be adjusted with throttle 125, which is controlled by controller 12. An ignition spark may be provided to combustion chamber 30 via spark plug 92 in response to a spark signal from controller 12. Alternatively, spark plug 92 may be omitted for a compression ignition engine. Further, controller 12 may activate fuel injector 65 during the engine operation so that a desired air-fuel ratio mixture is formed when ignition power is supplied to spark plug 92 by ignition system 88. Controller 12 controls the amount of fuel delivered by fuel injector 65 so that the air-fuel ratio mixture in chamber 30 may be selected to be substantially at (or near) stoichiometry, a value rich of stoichiometry, or a value lean of stoichiometry.

Controller 12 is shown in FIG. 1 as a conventional microcomputer including: microprocessor unit 102, input/output ports 104, an electronic storage medium of executing programs and calibration values, shown as read-only memory chip 106 in this particular example, random access memory 108, keep alive memory 110, and a conventional data bus.

Controller 12 is shown receiving various signals from sensors coupled to engine 10, in addition to those signals previously discussed, including: measurement of inducted mass air flow (MAF) from mass air flow sensor 117; accelerator pedal position from pedal position sensor 119; engine coolant temperature (ECT) from temperature sensor 112 coupled to cooling sleeve 114; a profile ignition pickup signal (PIP) from Hall effect sensor 118 coupled to crankshaft 40 giving an indication of engine speed (RPM); and absolute Manifold Pressure Signal (MAP) from sensor 122. Engine speed signal RPM is generated by controller 12 from signal PIP in a conventional manner and manifold pressure signal MAP provides an indication of engine load.

An exhaust gas recirculation (EGR) passage 130 is shown communicating with exhaust manifold 48 and intake manifold 44. The amount of EGR supplied to the intake manifold may be adjusted by EGR valve 134, which is in communication with controller 12. Further, controller 12 may receive a signal from EGR sensor 132, which may be configured to measure temperature or pressure of the exhaust gas within the EGR passage.

Exhaust gas oxygen sensor 76 is shown coupled to exhaust manifold 48 upstream of exhaust after-treatment system 70. Exhaust gas oxygen sensor 76 may be configured to provide a signal to controller 12, which indicates whether exhaust air-fuel ratio is either lean of stoichiometry or rich of stoichiometry. Exhaust after-treatment system 70 may include a catalytic converter, a lean $NO_x$ trap, and/or any other suitable treatment device. Exhaust after-treatment sensor 77 may be configured to provide a signal to controller 12 indicative of the condition of the exhaust after-treatment system 70 and may include measurement of temperature, pressure, etc.

$NO_x$ sensor 98 is shown coupled to exhaust manifold 48 downstream of exhaust after-treatment system 70. $NO_x$ sensor 98 may be configured to output a signal to controller 12 in response to a detected concentration of $NO_x$ in the engine exhaust, as will be described in more detail below. $NO_x$ sensor 98 may also be configured to receive a signal from controller 12, such as a control signal for controlling a temperature of the sensor, a voltage applied to electrodes in the sensor, etc. In an alternative embodiment, sensor 76 may be configured to measure the concentration of other species besides $NO_x$, including but not limited to $O_2$, CO, $H_2O$, $SO_x$, and other oxygen-containing gases.

$NO_x$ sensor 98 may be used both for control of the after-treatment system and for on-board diagnostics (OBD) to ensure the vehicle does not exceed the $NO_x$ emissions standards. One example of a $NO_x$ sensor is disclosed in U.S. Pat. No. 5,288,375. While many variations of $NO_x$ sensors exist, most sensors utilize a system which seeks to remove an interfering species from a sample gas prior to measuring the analyte. For example, for a $NO_x$ sensor, the interfering species may be $O_2$.

Figure 2:
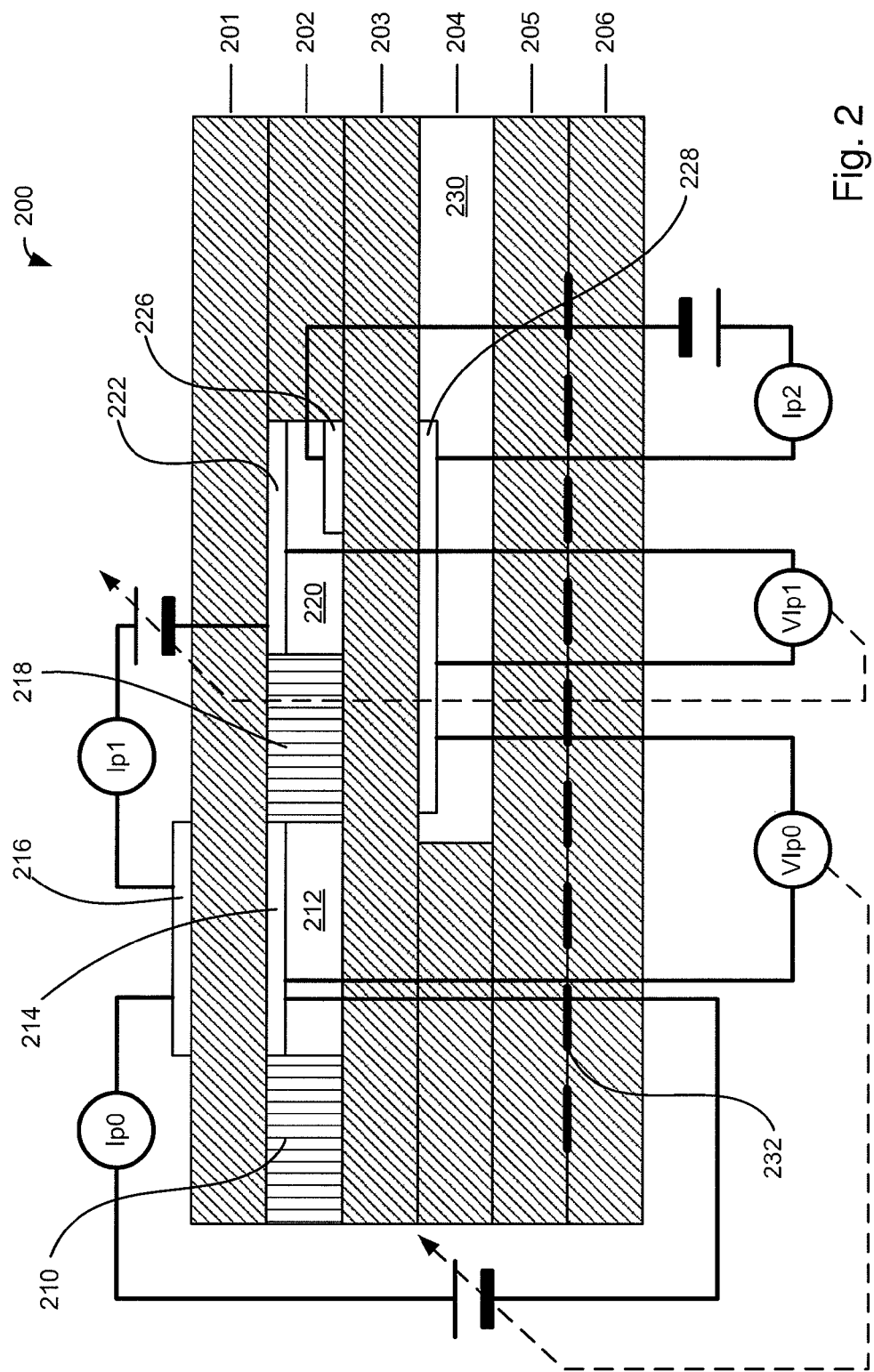
FIG. 2 is a schematic depiction of a first exemplary embodiment of a $NO_x$ sensor.

FIG. 2 shows a schematic view of an exemplary embodiment of a $NO_x$ sensor configured to measure a concentration of $NO_x$ gases in an emissions stream. The term $NO_x$ as used herein may refer to any combination of nitrogen and oxygen, including but not limited to NO and $NO_2$. Sensor 200 comprises a plurality of layers of one or more ceramic materials arranged in a stacked configuration. These layers of ceramic materials are depicted as layers 201, 202, 203, 204, 205 and 206. Layers 201-206 may be formed from any suitable material, including but not limited to oxygen ion conductors such as zirconium oxide-based materials. Further, in some embodiments, a heater 232 may be disposed between the various layers to increase the ionic conductivity of the layers. While the depicted $NO_x$ sensor is formed from six ceramic layers, it will be appreciated that the $NO_x$ sensor may include any other suitable number of ceramic layers.

Layer 202 includes a material or materials creating a first diffusion path 210. First diffusion path 210 is configured to introduce exhaust gases into a first internal cavity 212 via diffusion. A first pair of pumping electrodes 214 and 216 is disposed in communication with internal cavity 212, and is configured to electrochemically pump a selected exhaust gas constituent from internal cavity 212 through layer 201 and out of sensor 200. Generally, the species pumped from internal cavity 212 out of sensor 200 may be a species that may interfere with the measurement of a desired analyte. In a $NO_x$ sensor, oxygen can potentially interfere with the measurement of $NO_x$ at a measuring electrode, as oxygen is dissociated and pumped at a lower potential than $NO_x$. Therefore, where oxygen and $NO_x$ are both present at an electrode configured to measure $NO_x$ concentration, the resulting output signal includes contributions from ionic current caused by the dissociation of both $NO_x$ and $O_2$. Removal of the oxygen from the analytic exhaust gas sample in sensor 200 may allow $NO_x$ concentration to be measured substantially without interference from oxygen.

First diffusion path 210 may be configured to allow one or more components of exhaust gases, including but not limited to oxygen and $NO_x$ gases, to diffuse into internal cavity 212 at a slower rate than the interfering component can be electrochemically pumped out by first pair of pumping electrodes 214 and 216. Pumping electrodes 214 and 216 may be referred to herein as a first pumping electrode configuration. In this manner, oxygen may be removed from first internal cavity 212 to reduce interfering effects caused by oxygen.

The process of electrochemically pumping the oxygen out of first internal cavity 212 includes applying an electric potential $V_{Ip0}$ across first pair of pumping electrodes 214, 216 that is sufficient to dissociate molecular oxygen, but not sufficient to dissociate $NO_x$. With the selection of a material having a suitably low rate of oxygen diffusion for first diffusion path 210, the ionic current Ip0 between first pair of pumping electrodes 214, 216 may be limited by the rate at which the gas can diffuse into the chamber, which is proportional to the concentration of oxygen in the exhaust gas, rather than by the pumping rate of first pair of pumping electrodes 214, 216. This may allow substantially all oxygen to be pumped from first internal cavity 212 while leaving $NO_x$ gases in first internal cavity 212.

Sensor 200 further includes a second internal cavity 220 separated from the first internal cavity by a second diffusion path 218. Second diffusion path 218 is configured to allow exhaust gases to diffuse from first internal cavity 212 into second internal cavity 220. A second pumping electrode 222 optionally may be provided in communication with second internal cavity 220. Second pumping electrode 222 may, in conjunction with electrode 216, be set at an appropriate potential $V_{Ip1}$ to remove any residual oxygen that was not removed by first pair of pumping electrodes and that diffused through second diffusion path 218, but not to dissociate and pump any $NO_x$ gases. Second pumping electrode 222 and electrode 216 may be referred to herein as a second pumping electrode configuration. Alternatively, second pumping electrode 222 may be configured to maintain a substantially constant concentration of oxygen within second internal cavity 220. In some embodiments, V0 may be approximately equal to V1, while in other embodiments V0 and V1 may be different. While the depicted embodiment utilizes electrode 216 to pump oxygen from first internal cavity 212 and from second internal cavity 220, it will be appreciated that a separate electrode (not shown) may be used in conjunction with electrode 222 to form an alternate pumping electrode configuration to pump oxygen from second internal cavity 220.

Sensor 200 further includes a measuring electrode 226 and a reference electrode 228. Measuring electrode 226 and reference electrode 228 may be referred to herein as a measuring electrode configuration. Reference electrode 228 is disposed at least partially within or otherwise exposed to a reference air duct 230. Measuring electrode 226 may be set at a sufficient potential relative to reference electrode to pump $NO_x$ out of second internal cavity 220. The sensor output is based upon the pumping current flowing through measuring electrode 226 and pumping electrode 228, which is proportional to the concentration of $NO_x$ in second internal cavity 220.

Figure 3:
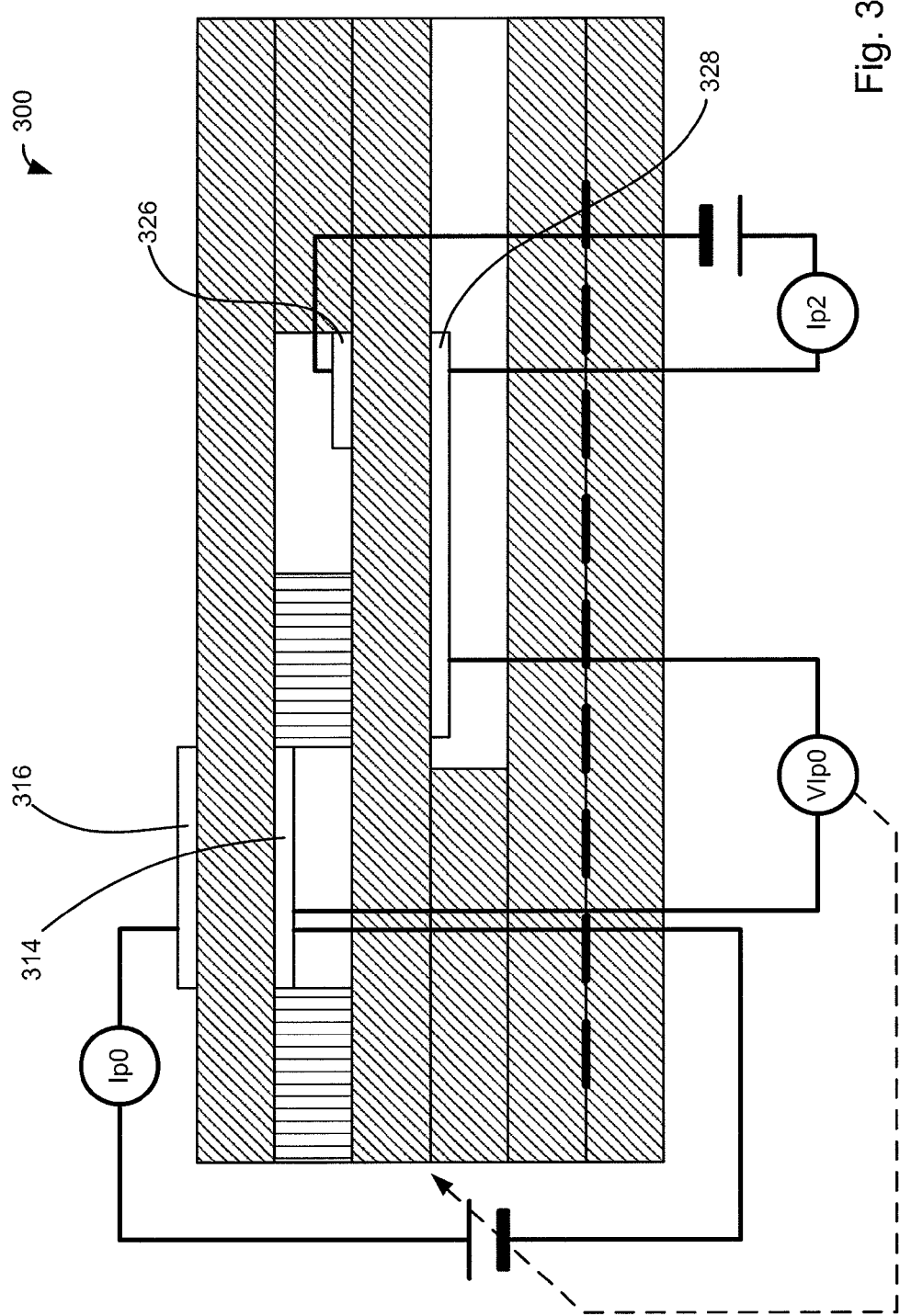
FIG. 3 is a schematic depiction of a second exemplary embodiment of a $NO_x$ sensor.

FIG. 3 shows an alternative embodiment of the $NO_x$ sensor 200 described above with reference to FIG. 2. Sensor 300 of FIG. 3 is shown having components similar to FIG. 2, while utilizing only one pair of pumping electrodes 314, 316 for removing an interfering species (i.e. pumping electrode 222 is not included). Because sensor 300 is shown having only one pair of pumping electrodes compared to the two pairs of sensor 200, the oxygen concentration reaching measuring electrodes 326, 328 may be different than the oxygen concentration reaching measuring electrodes 226, 228 in sensor 200. Furthermore, in some embodiments, a $NO_x$ sensor may include only one diffusion path and one internal cavity, thereby placing the pumping electrode and measuring electrode in the same internal cavity.

It should be understood that the sensors described above with reference to FIGS. 2 and 3 are non-limiting examples of $NO_x$ sensor configurations, and any other suitable sensor having any other configuration and/or materials may be used. Further, the methods disclosed herein may also be applied to sensors other than those used to detect $NO_x$, including but not limited to CO, $CO_2$, $SO_x$, and $H_2O$ sensors.

Figure 4:
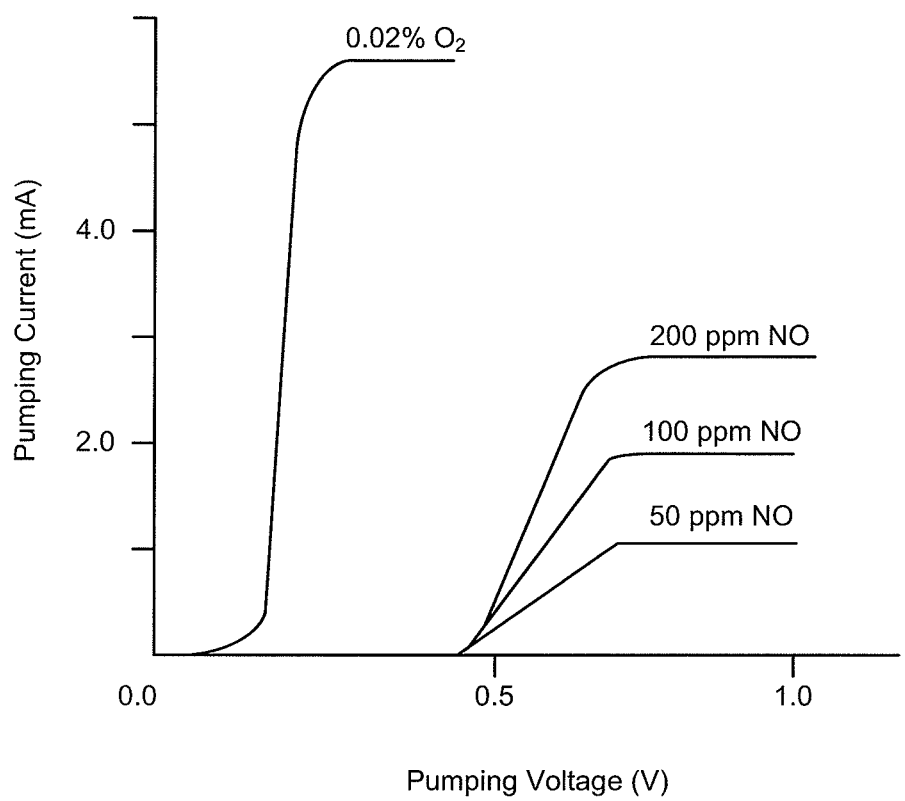
FIG. 4 is a graph depicting an exemplary relationship between pumping current and pumping voltage for $O_2$ and $NO_x$ of varying concentrations for an exemplary $NO_x$ sensor.

FIG. 4 shows a graph depicting a relationship between pumping current and pumping voltage for $O_2$ and $NO_x$ of varying concentrations for an exemplary $NO_x$ sensor. As shown in FIG. 4, $O_2$ is electrochemically dissociated at a lower pumping voltage than $NO_x$. Further, it can be seen that the ionic current resulting from the electrochemical dissociation of $O_2$ or $NO_x$ rapidly reaches a steady state pumping current, which is limited by the rates of diffusion of gases through diffusion path 210 as described above with reference to FIGS. 2 and 3. Therefore, the oxygen pumping potentials V0 and V1 may have any suitable value between the voltage at which oxygen pumping reaches a diffusion-limited steady state and at which $NO_x$ dissociation occurs. Likewise, the $NO_x$ pumping potential across electrodes 226 and 228 may have any suitable value at which $NO_x$ pumping occurs at a diffusion-limited state.

The sensitivity and accuracy of a $NO_x$ sensor may be affected by baseline drift, in which the baseline output (i.e. the output at 0 ppm $NO_x$) of the sensor drifts over time. However, the suitability of a sensor for a selected application may depend upon the accuracy of the sensor. For example, emissions standards for heavy-duty vehicles may require constant emission $NO_x$ levels not to exceed approximately 10 ppm. However, due at least in part to baseline drift, the accuracy of a conventional $NO_x$ sensor may be on the order of ±10 ppm $NO_x$. This level of uncertainty may therefore be too high, for example, to ensure that a vehicle meets applicable $NO_x$ emission regulations.

Figure 5:
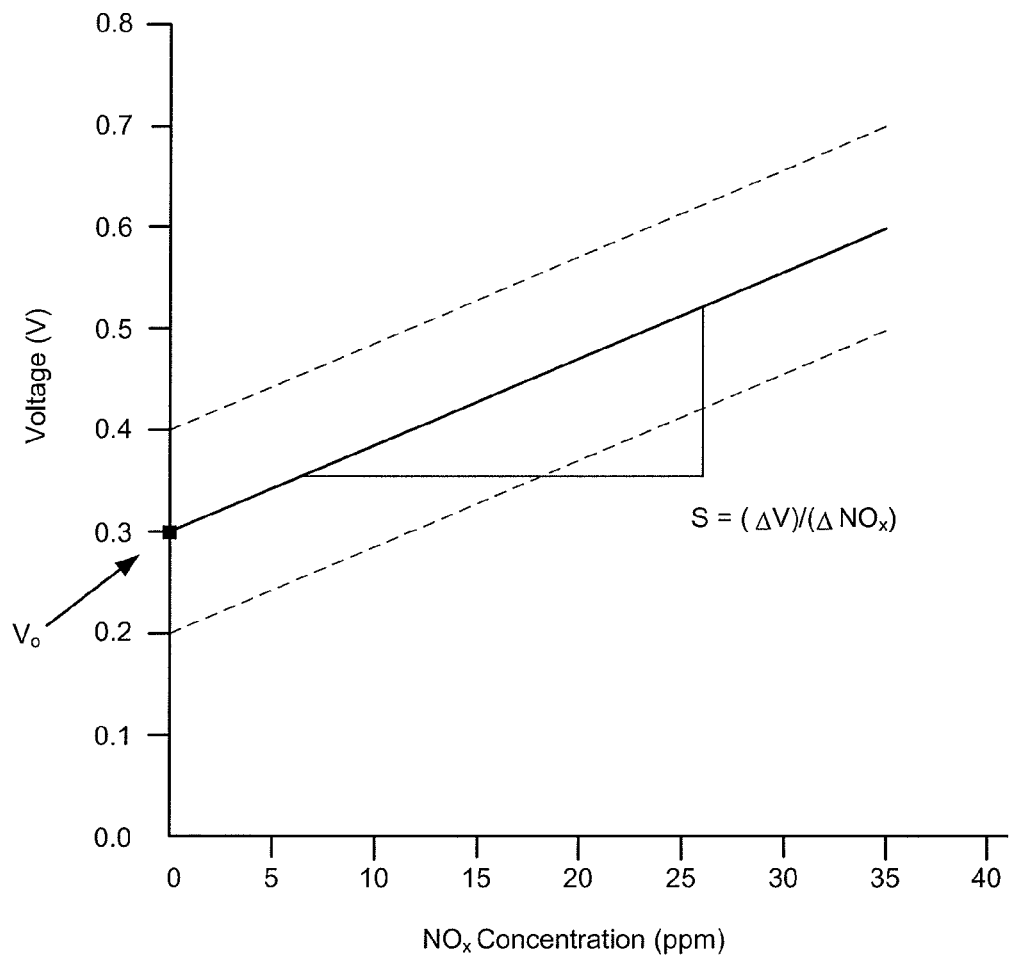
FIG. 5 is a graph depicting an exemplary relationship between $NO_x$ concentration and output voltage for an exemplary $NO_x$ sensor.

FIG. 5 shows a graph depicting the relationship between $NO_x$ concentration and output voltage for a typical commercially available $NO_x$ sensor. Specifically, FIG. 5 shows a linear relationship, as denoted by the solid black line, between output voltage (vertical axis) and $NO_x$ concentration (horizontal axis). Further, two broken lines are shown corresponding to the upper and lower variations in $NO_x$ reading based on a ±10 ppm $NO_x$ uncertainty. While the actual outputs for different sensors may differ from the outputs shown in FIG. 5, $NO_x$ sensors generally output a voltage that exhibits characteristics similar to that shown in FIG. 5, where the slope of the output response graph represents the sensitivity of the sensor and may be described by $S=(\Delta V)/(\Delta NO_x)$.

As a $NO_x$ sensor ages, the value of the baseline for the sensor may increase or otherwise drift. The ±10 ppm uncertainty in conventional $NO_x$ sensors may arise from such uncertainties in Vo. Physical causes for this drift may include, but are not limited to, currents in the solid electrolyte caused by ionic impurities and/or conductive paths through the electrolyte. As demonstrated by the slope of the sensor response graph in FIG. 5, variations in the baseline value of Vo may affect the $NO_x$ sensor output, particularly at low $NO_x$ concentrations typically found in modern engine exhaust. Therefore, eliminating or reducing uncertainties in the variation of the baseline voltage (Vo) may help to achieve to achieve a desired accuracy, for example, ±5 ppm $NO_x$, and may therefore allow conventional $NO_x$ sensors to be used for more accurate measurements in modern emissions and on-board diagnostics systems.

One possible approach for obtaining an updated value for the baseline voltage is to measure the sensor output voltage when engine operating conditions generally lead to absence of $NO_x$ in the exhaust gas (for example, while operating at a rich air/fuel ratio) to obtain an updated baseline output value, and then to store the updated baseline value in memory for use in interpreting the output from $NO_x$ sensors 200 and 300, among others. Although this approach may give an accurate and updated value for the baseline voltage, there may be an uncertainty whether the environment is truly at a 0 ppm $NO_x$ level during baseline updating.

To overcome such problems, the potentials across the first pumping electrodes 214, 216 and the second pumping electrodes 222, 216 (if applicable) may be occasionally adjusted to a sufficiently high potential to pump $NO_x$. In this mode of operation, $NO_x$ may be substantially completely pumped out of internal cavities 212 and 220 before reaching measuring electrode 226. This may help to ensure that substantially 0 ppm $NO_x$ reaches measuring electrode 226 when obtaining an updated baseline output measurement. After establishing the updated baseline output measurement, the pumping electrodes may be returned to their respective oxygen-pumping potentials for normal sensor operation. Therefore, using this approach, an updated baseline output voltage may be obtained for a $NO_x$ sensor even in the presence of high $NO_x$ levels, such as during lean operation of the vehicle. This approach therefore may be used in conjunction with conventional, commercially available $NO_x$ sensors to improve the accuracy of these sensors.

The potentials of the various electrodes in $NO_x$ sensors 200 and 300 may be adjusted in any suitable manner to remove $NO_x$ from cavities 212 and 220 before reaching measuring electrode 226. For example, in some embodiments, sensors 200 and 300 may be operated in a "normal" or analytical mode, as described above with reference to FIG. 2, for a majority of the sensor operation, thereby measuring $NO_x$ levels at the measuring electrode. Occasionally, the sensor may be operated in an update mode wherein the potentials of the oxygen pumping electrodes are changed so that $NO_x$ is pumped out of the first and second internal cavities. The sensor may be operated in the update mode at any suitable time and/or interval. For example, the update mode may be used at the beginning of a drive cycle, when the engine is operating under selected operating conditions, and/or at a scheduled time interval, engine cycle interval, etc.

Figure 6:
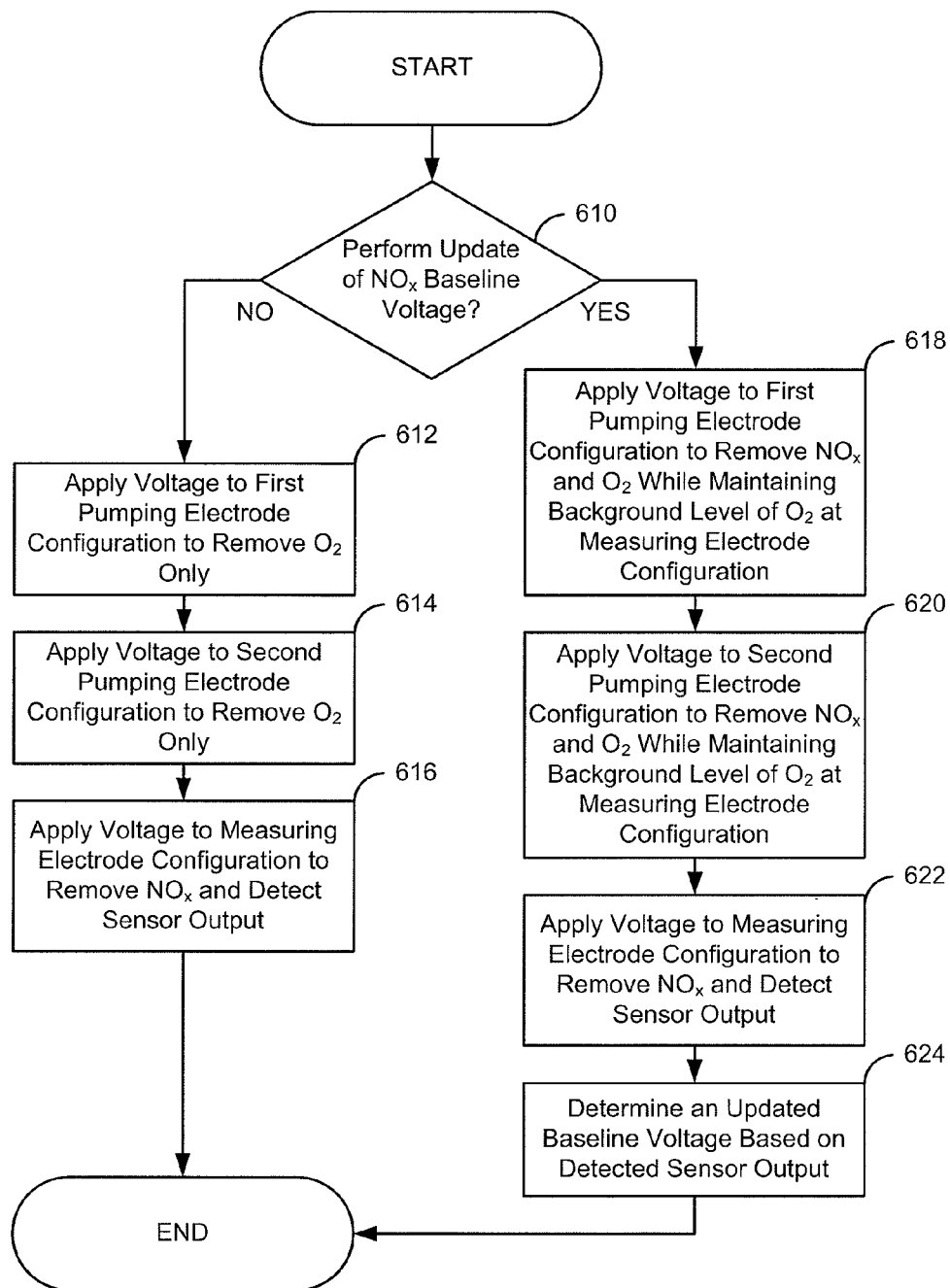
FIG. 6 is a flow diagram showing an exemplary embodiment of a method for determining a baseline voltage of a $NO_x$ sensor.

FIG. 6 shows, generally at 600, a flow chart of an exemplary embodiment of a method for updating a gas sensor baseline output. Method 600 may be performed by controller 12 via the execution of instructions stored in memory on controller 12 by processor 102, or in any other suitable manner. Method 600 begins by determining, at 610, whether an update of the $NO_x$ baseline output is requested. If an update of the baseline output is not requested, then method 600 performs processes 612 through 616 corresponding to the normal analytical operation of the sensor wherein $NO_x$ in the exhaust gas is measured. More specifically, method 600 includes applying voltages to the first and second pumping electrode configurations at 612 and 614, respectively, to remove $O_2$ from the internal cavities without removing $NO_x$. Next, method 600 includes, at 616, applying a voltage to the measuring electrode configuration (i.e. measuring electrode and reference electrode) to remove $NO_x$, and detecting an output of the sensor corresponding to the concentration of $NO_x$ in the exhaust gas. It will be appreciated that a baseline output update may be requested or otherwise triggered at any suitable time or interval, by any suitable event, or in any other suitable manner. In general, baseline drift may occur relatively slowly with time, and therefore the sensor may not require constant or frequent baseline updating. Updating may be requested, for example, soon after the sensor reaches its start-up point at the beginning of a drive cycle. This may help to ensure the accuracy of $NO_x$ measurements made during that drive cycle.

Referring again to FIG. 6, if the answer at process 610 is yes, method 600 includes performing processes 618 through 624, wherein the sensor baseline output is updated. More specifically, a voltage sufficient to remove both $O_2$ and $NO_x$ while maintaining the background level of $O_2$ at the measuring electrode configuration is applied at 618 to the first pumping electrode configuration and possibly at 620 to the second pumping electrode configuration (if present), under the constraint that the background level of $O_2$ at the $NO_x$ measuring electrode configuration is maintained at the same level as is present during "normal sensor operation" (processes 612 through 616). Further, method 600 includes applying, at 622, a voltage to the measuring electrode configuration sufficient to remove $NO_x$, and detecting an output of the sensor corresponding to the baseline sensor output. Next, at process 624, the sensor baseline is adjusted or updated based on the detected sensor output of process 622. This may involve, for example, storing the detected baseline output in memory on controller 12. This updated baseline output may be used to scale, offset, or otherwise adjust an output later received from the $NO_x$ sensor to compensate for any baseline shift.

Under some engine operating conditions, a substantial concentration of $O_2$ may be present in the exhaust gas such that a small concentration of $O_2$ may reach a measuring electrode while operating the sensor in its "normal mode of operation". Furthermore, the amount of oxygen reaching a measuring electrode may be dependent upon sensor configuration or age. For example, because sensor 300 includes only one pair of pumping electrodes, it is possible that a greater amount of residual $O_2$ may reach the measuring electrode relative to sensor 200. The residual $O_2$ reaching the $NO_x$ sensing electrode affects the sensor output, as it is electrochemically pumped at the $NO_x$ measuring electrode configuration along with the oxygen from $NO_x$. If this small concentration of $O_2$ at the $NO_x$ measuring electrode configuration changes during the baseline update procedure, then an inaccurate baseline output update value may be obtained.

Figure 7:
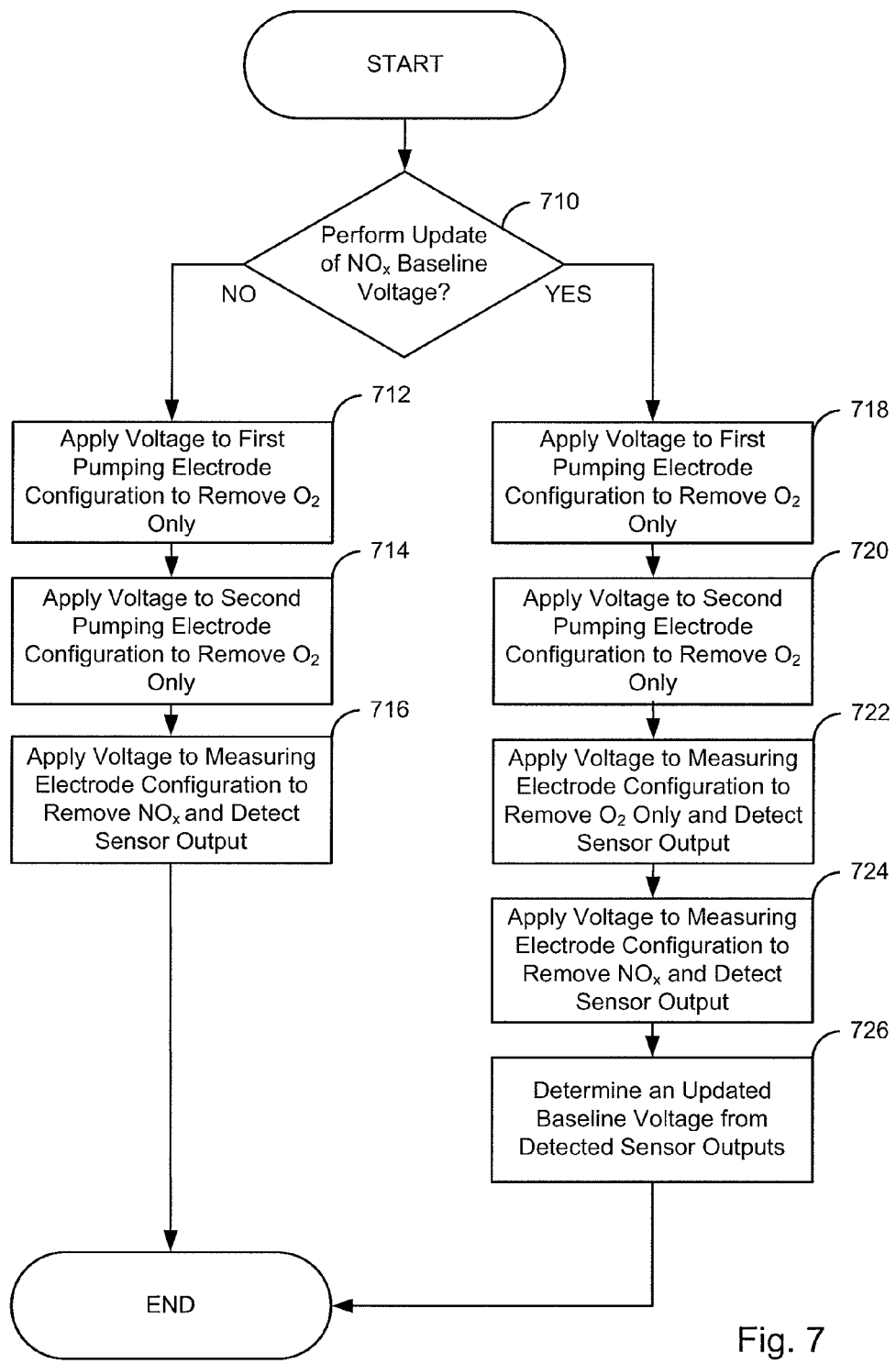
FIG. 7 is a flow diagram showing another exemplary embodiment of a method for determining a baseline voltage of a $NO_x$ sensor.

Therefore, an alternate baseline update mode may be utilized if sensors 200 or 300 are operated in the previously described baseline update mode under conditions that may cause the residual oxygen reaching the measuring electrode configuration to change. This alternative approach may be used to compensate for the possible presence of residual oxygen at measuring electrode 226. Any suitable method may be used to compensate for the possible presence of oxygen at measuring electrode 226 while operating sensor 200 or 300 in an update mode. FIG. 7 shows, generally at 700, a flow chart of an exemplary embodiment of a method for determining a sensor baseline that compensates for residual $O_2$ (or other interfering species) reaching the measuring electrode. Method 700 first includes determining, at 710, whether an update of the $NO_x$ baseline voltage is requested. If the answer is no, then method 700 proceeds to processes 712 through 716 corresponding to the normal operation of the sensor wherein $NO_x$ in the exhaust gas is measured. For example, processes 712 and 714 include applying a voltage to the first and second pumping electrode configurations to remove $O_2$ from the internal cavities without removing $NO_x$. Further, process 716 includes applying a voltage to the measuring electrode configuration (measuring electrode and reference electrode) to remove $NO_x$ and detecting an output of the sensor corresponding to the concentration of $NO_x$ in the exhaust gas.

Alternatively, if the answer at process 710 is yes, then method 700 proceeds to perform processes 718 through 724, wherein the sensor baseline is updated while considering an amount of residual $O_2$ reaching the measuring electrode. For example, processes 718 and 720 involve applying a voltage to the first and second pumping electrode configurations to remove $O_2$ from the internal cavities without removing $NO_x$. Next, at process 722, a voltage is applied to the measuring electrode configuration sufficient to remove $O_2$ but not $NO_x$, and a sensor output corresponding to the amount or concentration of residual $O_2$ at the measuring electrode is detected. Next, process 724 includes applying a voltage to the measuring electrode configuration to remove $NO_x$ and detecting an output of the sensor corresponding to an amount of oxygen removed by the measuring electrode configuration. Further, at process 726, the measured sensor baseline is updated based upon the detected sensor outputs, as described above for method 600. In some embodiments, the detected output of process 722 corresponding to the concentration of residual $O_2$ at the measuring electrode may be subtracted from the detected output of process 724 corresponding to the output of the sensor at the higher measuring electrode potential, thereby determining the sensor baseline corresponding to approximately 0 ppm $NO_x$.

In some embodiments, the methods described above with reference to FIGS. 6 and 7 may be performed at any time during vehicle operation. In other embodiments, an updated baseline may be determined when the engine is operating at substantially steady state (for example, during engine shut-off or deceleration fuel shut-off) or at idle (i.e. when a substantially constant gas sample is available). This may help to avoid transient effects such as rapid pressure variation. Since the methods of updating the sensor baseline can take a finite amount of time to perform, during which the sensor may not be measuring the analyte concentration in the gas sample, an update of the baseline may be performed when a measurement of analyte is not needed (for example, during engine shut-off, deceleration fuel shut-off, idle, etc.), thereby limiting the amount of time the sensor is operating in a baseline update mode.

After updating the $NO_x$ sensor baseline output, controller 12 may use the updated output value in combination with a $NO_x$ sensor reading to determine a $NO_x$ concentration in the engine exhaust, and to control an engine operating parameter in response to determining the $NO_x$ concentration with the updated baseline output value. Examples of engine operating parameters or conditions that may be adjusted include, but are not limited to, an amount of air supplied to the engine, an amount of fuel supplied to the engine, a combustion timing, a valve timing, a turbocharging condition or parameter, a supercharging condition or parameter, a throttle condition or parameter, and/or a $NO_x$ trap condition or parameter.

It will be understood that the example control routines disclosed herein can be used with various sensor configurations. The specific routines described herein may represent one or more of any number of processing strategies such as event-driven, interrupt-driven, multi-tasking, multi-threading, and the like. As such, various steps or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated steps or functions may be repeatedly performed depending on the particular strategy being used. Further, the described steps may graphically represent code to be programmed into a computer readable storage medium.

It will be appreciated that the configurations and routines disclosed herein are exemplary in nature, and that these specific embodiments are not to be considered in a limiting sense, because numerous variations are possible. The subject matter of the present disclosure includes all novel and nonobvious combinations and subcombinations of the various systems and configurations, and other features, functions, and/or properties disclosed herein. The following claims particularly point out certain combinations and subcombinations regarded as novel and nonobvious. These claims may refer to "an" element or "a first" element or the equivalent thereof. Such claims should be understood to include incorporation of one or more such elements, neither requiring nor excluding two or more such elements. Other combinations and subcombinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A method of operating a $NO_x$ sensor, wherein the sensor includes a pumping electrode configuration and a measuring electrode configuration, the method comprising:
    operating in a first update operating mode responsive to determining that the $NO_x$ sensor is operating under first conditions that cause an absence of $NO_x$ in exhaust gas, the first update operating mode including removing $NO_x$ and at least a portion of $O_2$ from the sensor;
    determining that the $NO_x$ sensor is operating under second conditions that cause a change in residual $O_2$ reaching the measuring electrode configuration; and
    responsive to the determining, operating in a second, alternate update operating mode, the second, alternate update operating mode including,
        applying a first measuring voltage across the measuring electrode configuration sufficient to electrochemically remove $O_2$ from the sensor without electrochemically removing $NO_x$ from the sensor; and
        applying a second measuring voltage across the measuring electrode configuration sufficient to electrochemically remove $NO_x$ from the sensor.

2. The method of claim 1, further comprising receiving a first output signal from the $NO_x$ sensor while applying the first measuring voltage, and receiving a second output signal from the $NO_x$ sensor while applying the second measuring voltage.

3. The method of claim 2, further comprising determining a difference between the first and the second output signals and storing said difference.

4. The method of claim 1, further comprising performing said method at least once during an engine drive cycle.

5. The method of claim 2, further comprising adjusting an operating condition of an engine based on at least one of the first and the second output signals.

6. The method of claim 5, wherein the operating condition of the engine includes at least one of an amount of air supplied to the engine, an amount of fuel supplied to the engine, a combustion timing, a valve timing, a turbocharging condition, a supercharging condition, a throttle condition, and a $NO_x$ trap condition.

7. A method of operating a $NO_x$ sensor, wherein the sensor includes a pumping electrode configuration and a measuring electrode configuration, the method comprising:
    applying a first pumping voltage across the pumping electrode configuration sufficient to electrochemically remove $NO_x$ and $O_2$ from the sensor;
    applying a first measuring voltage across the measuring electrode configuration sufficient to electrochemically remove $NO_x$ from the sensor;
    responsive to detecting no change in residual $O_2$ reaching the measuring electrode configuration, operating in a first update operating mode, the first operating mode including removing $NO_x$ and at least a portion of $O_2$ from the sensor; and
    responsive to detecting a change in residual $O_2$ reaching the measuring electrode configuration, operating in a second, alternate update operating mode, the second, alternate update operating mode including,
        applying a second measuring voltage across the measuring electrode configuration sufficient to electrochemically remove $O_2$ from the sensor without electrochemically removing $NO_x$ from the sensor; and
        applying a third measuring voltage across the measuring electrode configuration sufficient to electrochemically remove $NO_x$ from the sensor.

* * * * *